US00PP10513P

United States Patent [19]

Lemon

[11] Patent Number: Plant 10,513

[45] Date of Patent: Jul. 21, 1998

0

[54] VARIETY OF GERANIUM NAMED 'GLOBAL LIGHT LILAC'

[75] Inventor: David Lemon, Lompoc, Calif.

[73] Assignee: John Bodger & Sons Company, So. El Monte, Calif.

[21] Appl. No.: 724,699

[22] Filed: Oct. 1, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 7,358 10/1990 Guillou et al. ..... Plt./87.12

P.P. 7,721 11/1991 Guillou et al. ..... Plt./87.12

P.P. 8,327 7/1993 Schumann ..... Plt./87.12

*Primary Examiner*—Howard J. Locker

*Attorney, Agent, or Firm*—Fulwider Patton Lee & Utecht, LLP

[57] ABSTRACT

The cultivar is characterized by its medium green foliage and pale orchid color bloom having a small deep purple eye near the center. Its relatively strong growth habit, quick rooting time and continuous, relatively large flowering provide for superb cuttings and also for quick recovery following wet weather conditions. The blooms exhibit good post-harvest quality and the cascading nature of the cultivar makes it suitable for a trailing finish product.

1 Drawing Sheet

BACKGROUND OF THE NEW PLANT

The present invention comprises a new and distinct cultivar of *Pelargonium×peltatum* known by the varietal name Global Light Lilac (Oglevee No. 3182, Bodger No. 3GM 12-2). The new variety was discovered in a selective breeding program by David Lemon at Bodger Seeds, Ltd., Lompoc, Calif. The new variety is a selection from the crossing of Nicole (U.S. Plant Pat. No. 7,358) which is characterized by a candy pink flower with Iris Bader (Bodger No. 1 GM 320 unpatented) which has a large magenta-rose colored semi-doubled flower having darker marking as distinguished from the claimed cultivar which has a pale orchid color bloom having a deep purple eye.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° Fahrenheit night temperature, 68° Fahrenheit day temperature, 72° Fahrenheit vent temperature and grown in a soilless media of constant fertilizer 200–250 parts per million of nitrogen and potassium has a response time of six weeks from the rooted cutting to a flowering plant in a 10.0 cm pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted on approximately Feb. 1, 1996 and flowering on approximately Mar. 14, 1996 under full light and greenhouse, and colorings were taken indoors under 200–220 foot candles of fluorescent cool white light using The R.H.S. Colour Chart of The Royal Horticultural Society of London.

The Plant

Classification:
- *Botanical.*—*Pelargonium×peltatum.*
- *Commercial.*—Ivy Geranium Global Light Lilac.

Form: Cascading mound.
- *Height.*—18.0–24.0 cm from media surface.
- *Growth.*—Upright mound with cascading side growth, free and early flowering; free branching.
- *Strength.*—Does not need artificial support while allowing outer branches to cascade.

Foliage: Stalked leaf attachment; zone present.

Leaves:
- *Size.*—5.0–7.5 cm across.
- *Shape.*—Reniform; cordate base.
- *Margin.*—Pedately lobed.
- *Texture.*—Smooth; slightly reflective.
- *Color.*—Top: Green group 137B. Bottom: Yellow-green group 146C. Zone: Greyed-purple group 184A.
- *Ribs and veins.*—Palmate venation: Color: Yellow-green group 146C.

Petioles:
- *Length.*—5.0–7.0 cm.
- *Color.*—Yellow-green group 146C.

Stem:
- *Color.*—Yellow-green group 146C.
- *Internodes.*—3.0–5.5 cm in length.

The Bud (Umbel)

Shape: Elliptical cluster.

Size: 2.0–2.5 cm across.

Inflorescence

Blooming habit: Continuous, free and early.

Borne: Florets on pedicel; pedicel on peduncle; umbel 6–9 cm above foliage.

Closed florets:
*Bud size.*—1.0–1.5 cm in length; 5 mm in width.
Size:
*Fully open bloom.*—9.0–11.0 cm across.
Open florets:
*Form.*—Flat to slightly cupped.
*Color.*—Top: Purple group 77D with veining of red-purple group 74A. Bottom: Purple group 75C. Eye: Red-purple group 74A eye creates the appearance of a slight blotch near the middle.
*Petals.*—21–25 in number; separate, not united; margin entire.
*Size.*—6.0–7.0 cm across; about 12 florets appearing per umbel.
*Texture and appearance.*—Flowers are pale orchid with a deep purple eye above medium green foliage.
Petaloids:
*Quantity.*—4–6.
*Shape.*—Twisted.
*Color.*—Top: Purple group 77 D. Bottom: Purple group 75C.
Pedicel:
*Length.*—2.5–3.5 cm.
*Color.*—Yellow-green group 146C at bottom; Yellow-green group 147A at top.
Peduncle:
*Length.*—16–17 cm.
*Color.*—Yellow-green group 146C.
Persistence:
*Disease resistance.*—Not known.
*Lasting quality.*—Unknown.

Reproductive Organs

Stamens:
*Anthers.*—Length: 1.0–1.3 cm.
*Filaments.*—Length: 1.0–1.3 cm. Color: White at base; orchid at tip.
*Pollen.*—Light to dark golden brown.
Pistils:
*Number.*—One.
*Length.*—5–6 mm.
*Stigma.*—Color: Red purple.
*Style.*—Length: 1–2 mm; 5 parted.
Ovaries:
*Color.*—Green, pubescent, superior.
*Length.*—4–5 mm.
Fruit: None.

General Characteristics

Global Light Lilac is an improvement over the current variety Yvette (U.S. Plant Pat. No. 7,721) which has a light purple flower with a blotch of maroon near the center. Global Light Lilac exhibits a similar color but has relatively larger florets, improved cutting production and rooting, is less sensitive to soluble salts and provides a well rounded trailing finish product.

I claim:

1. A new and distinct variety of Geranium plant, substantially as shown and described.

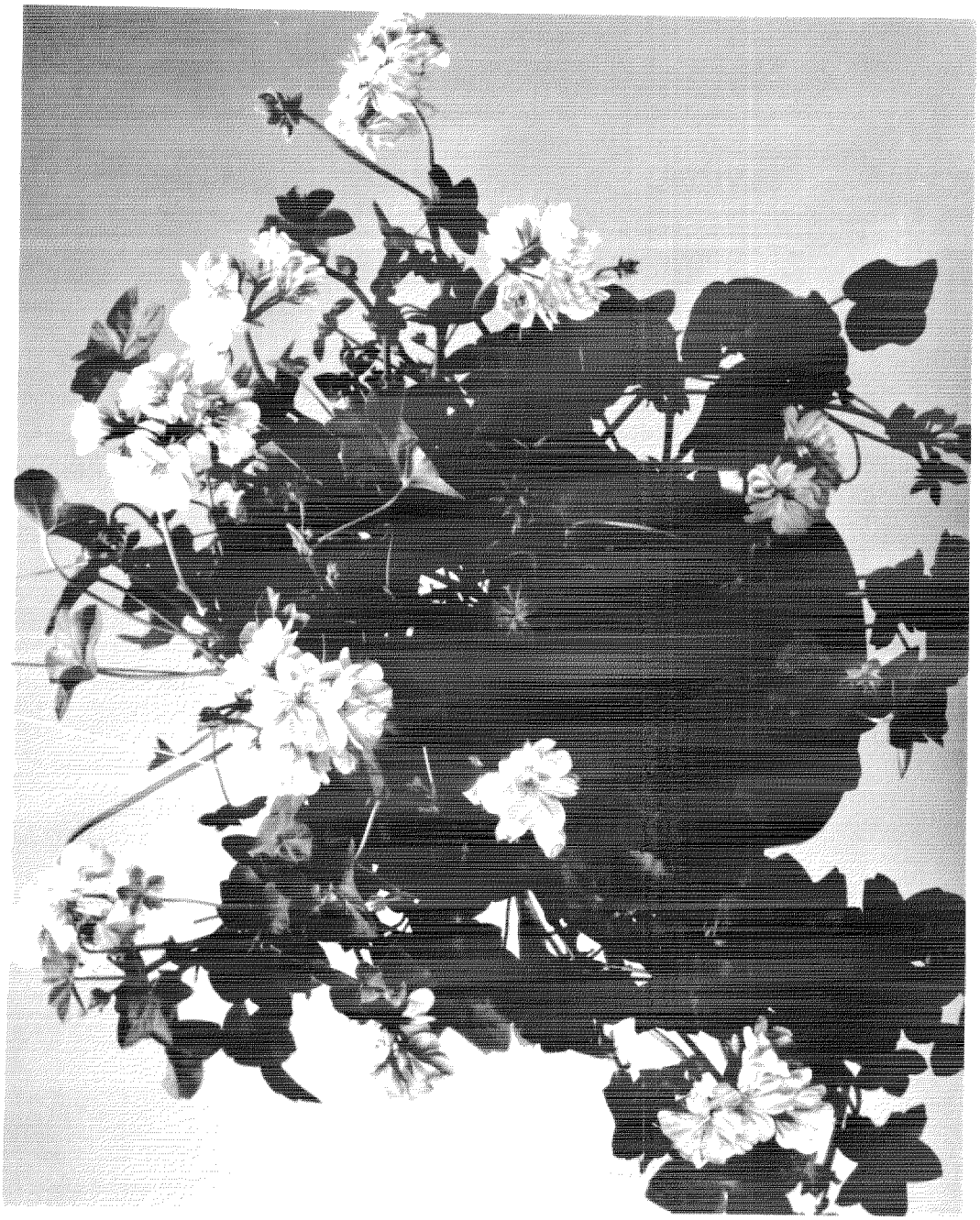

* * * * *